United States Patent [19]

Blum et al.

[11] 4,317,778

[45] Mar. 2, 1982

[54] PREPARATION OF MALEIC ANHYDRIDE USING FLUIDIZED CATALYSTS

[75] Inventors: Patricia R. Blum, Macedonia; Mark L. Nicholas, Cleveland, both of Ohio

[73] Assignee: Standard Oil Company (SOHIO), Cleveland, Ohio

[21] Appl. No.: 220,624

[22] Filed: Dec. 29, 1980

[51] Int. Cl.³ .......................................... C07D 307/60
[52] U.S. Cl. ................................ 260/346.75; 252/437
[58] Field of Search ................................... 260/346.75

[56] References Cited

U.S. PATENT DOCUMENTS

| | | | |
|---|---|---|---|
| 2,773,921 | 12/1956 | Rylander, Jr. et al. | 585/466 |
| 3,238,254 | 3/1966 | Kerr | 562/535 |
| 3,474,041 | 10/1969 | Kerr | 252/411 |
| 3,888,886 | 6/1975 | Young et al. | 260/346.75 |
| 3,905,914 | 9/1975 | Jurewicz et al. | 252/437 |
| 3,907,707 | 9/1975 | Raffelson et al. | 252/437 |
| 3,931,046 | 1/1976 | Weinstein et al. | 252/429 R |
| 3,932,305 | 1/1976 | Jurewicz et al. | 252/429 R |
| 3,975,300 | 8/1976 | Burress | 252/435 |
| 4,013,586 | 3/1977 | Dolan et al. | 252/437 |
| 4,043,943 | 8/1977 | Schneider | 252/437 |
| 4,149,992 | 8/1979 | Mount et al. | 252/435 |
| 4,179,404 | 12/1979 | Barone | 252/435 |

*Primary Examiner*—Henry R. Jiles
*Assistant Examiner*—Bernard Dentz
*Attorney, Agent, or Firm*—Joseph G. Curatolo; Herbert D. Knudsen; Larry W. Evans

[57] ABSTRACT

A process is provided for preparing fluid bed catalysts containing the mixed oxides of vanadium and phosphorus prepared from a mixed phosphoric acid source. A pentavalent vanadium compound is introduced into an organic liquid capable of reducing the vanadium, the vanadium is contacted with the mixed phosphoric acid source, the resulting catalyst precursor is comminuted, introduced into water to form an aqueous slurry and spray dried to form microspheroidal, fluidizable particles.

16 Claims, No Drawings

PREPARATION OF MALEIC ANHYDRIDE USING FLUIDIZED CATALYSTS

CROSS-REFERENCE TO RELATED APPLICATIONS

The invention of the subject application is disclosed, but not claimed, in copending application U.S. Ser. No. 221,670 directed to Preparation of Fluid Bed Catalysts Containing the Mixed Oxides of Vanadium and Phosphorus by E. C. Milberger, M. F. Lemanski and G. S. Spitnale, and assigned to our common assignee.

BACKGROUND OF THE INVENTION

This invention relates to a process for preparing fluid bed catalysts useful in the production of dicarboxylic acid anhydrides by the oxidation of hydrocarbons. More particularly it is directed to the preparation of fluid bed catalysts suitable for producing maleic anhydride from 4-carbon atom hydrocarbons, such as n-butane, n-butenes, 1,3 butadiene or a mixture thereof.

Catalysts containing vanadium and phosphorus oxides have been used in the oxidation of 4-carbon atom hydrocarbons, such as n-butane, n-butenes, 1,3 butadiene or mixtures thereof with molecular oxygen or oxygen-containing gas to produce maleic anhydride. Conventional methods of preparing these catalysts involve combining a vanadium compound, a phosphorus compound, and if desired, promoter element compound in a reducing medium under conditions which will provide vanadium in a valence state below +5 to form catalyst precursors capable of being converted to an oxide. The catalyst oxide precursor is then recovered and calcined to provide active catalytic material.

It has been taught in the art that various pentavalent and trivalent phosphorus compounds are satisfactory phosphorus components for use in the preparation of mixed vanadium phosphorus oxide catalysts. Orthophosphoric acid has been designated by some in the art as a preferred component.

U.S. Pat. No. 3,238,254 to Kerr lists the use of various phosphorus compounds such as metaphosphoric acid, triphosphoric acid, pyrophosphoric acid, orthophosphoric acid, phosphorus pentoxide, phosphorus oxyiodide, ethyl phosphate, methyl phosphate, amine phosphate, phosphorus pentachloride, phosphorus trichloride, phosphorus oxybromide, and the like, in the preparation of catalysts containing the mixed oxides of vanadium and phosphorus.

U.S. Pat. No. 3,474,041 to Kerr contains the above disclosure, and additionally discloses that vanadium phosphorus catalysts may be reactivated and stabilized by adding to the catalyst an organophosphorus compound.

U.S. Pat. No. 3,907,707 to Raffelson et al., 4,149,992 to Mount et al. and 4,179,404 to Barone disclose the preparation of vanadium phosphorus oxide catalysts using trivalent phosphorus compounds such as orthophosphorous acid, pyrophosphorous acid, methaphosphorous acid and hypophosphorous acid. Other phosphorus sources may include phosphorus trioxide and organic phosphites. A pentavalent phosphorus compound additionally could be utilized.

U.S. Pat. No. 4,013,586 to Dolan et al. discloses the preparation of vanadium phosphorus oxide catalysts using organo phosphonates as the source of phosphorus. A pentavalent phosphorus compound additionally could be utilized.

U.S. Pat. Nos. 3,888,886; 3,905,914; 3,931,046; 3,932,305 and 3,975,300 disclose the testing of promoted vanadium phosphorus oxide catalysts for maleic anhydride production from butane in one inch diameter fluid bed reactors. In most instances, the catalysts were prepared by forming the catalyst precursor in aqueous media (in U.S. Pat. No. 3,975,300 the precursor was formed in a paste of a vanadium compound, a phosphorus compound and an organic reducing agent), drying and thereafter grinding and sieving the precursor to a powder of about 74 to 250 microns size. This manner of preparation, however, does not obtain the uniform, microspheroidal catalyst particles preferred for successful fluid bed operation.

U.S. Pat. No. 4,043,943 discloses the preparation of the catalyst precursor in a liquid organic medium, preferably anhydrous, wherein the vanadium compound is reduced and solvated by gaseous HCl followed by reaction with the phosphorus compound.

The preparation of oxidation catalysts containing the mixed oxides of vanadium and phosphorus is disclosed in copending U.S. Ser. No. 106,786, assigned to our common assignee, now U.S. Pat. No. 4,244,879, wherein a vanadium compound is at least partially solubilized in an organic liquid medium capable of reducing at least a portion of the vanadium to a +4 valence state, and unsolubilized vanadium having a particle size larger than about 0.1 mm diameter is removed from the medium before addition of a phosphorus-containing compound.

The preparation of such catalysts is disclosed in copending U.S. Ser. No. 146,971, assigned to our common assignee, wherein partial reduction of a pentavalent vanadium compound is effected in the presence of a phosphorus compound in an organic liquid medium capable of reducing the vanadium.

It has been disclosed in copending U.S. Ser. No. 220,629 directed to the Preparation of Vanadium Phosphorus Oxide Catalysts Using a Mixed Phosphorus Source by P. R. Blum, E. C. Milberger, N. J. Bremer, D. E. Dria, and assigned to our common assignee, that vanadium phosphorus mixed oxide containing catalysts exhibit enhanced activity and selectivity to the production of maleic anhydride from 4-carbon atom hydrocarbons, such as n-butane, when such catalysts have been prepared from a mixed phosphorus source comprising orthophosphoric and pyrophosphoric acids. These catalysts are particularly effective when prepared in organic media.

As was discussed in Milberger et al., above, it had previously been found that contacting a vanadium phosphorus mixed oxide catalyst with water during preparation of the catalyst precursor resulted in diminution of surface area and activity of the catalyst for maleic anhydride production. In addition, contacting the calcined catalyst with water (below 100° C.) reduces the activity of the catalyst.

Although excellent fixed bed catalyst disclosed in Blum et al., above, may be prepared without contacting the catalyst precursor with water, the method disclosed by Milberger et al., above, for the preparation of microspheroidal fluid bed catalyst particles dictates contacting the catalyst precursor with water. We initially found that vanadium phosphorus mixed oxide catalyst precursors which had been prepared using a mixed orthophosphoric/pyrophosphoric acid source in organic liquid media, had a tendency when contacted with water for slurrying prior to spray drying, to partially dissolve, forming a thick, viscous slurry unsuitable for spray drying.

It is therefore an object of the present invention to provide a process for the preparation of fluidizable, microspheroidal catalysts containing the mixed oxides of vanadium and phosphorus, which catalysts have been prepared from a mixed phosphorus source of orthophosphoric and pyrophosphoric acid.

It is a further object of the present invention to provide a process for producing maleic anhydride from 4-carbon atom hydrocarbons utilizing fluid bed vanadium phosphorus mixed oxide catalysts prepared using a mixed phosphorus source of orthophosphoric and pyrophosphoric acid.

SUMMARY OF THE INVENTION

We have now found that excellent, fluidizable microspheroidal vanadium phosphorus mixed oxide-containing catalysts can be prepared using a mixed phosphorus source of orthophosphoric and pyrophosphoric acid in organic liquid media. The catalyst precursors from which the fluidizable catalysts are obtained, may be contacted with water to form an aqueous slurry suitable for spray drying, without deleterious effect. The fluidizable, microspheroidal catalyst obtained exhibits excellent activity for the production of maleic anhydride from 4-carbon atom hydrocarbons.

The process of the present invention provides a method to minimize the solubility of the catalyst precursor in water which possibly results from hydrolysis of pyrophosphate linkages incorporated into the catalyst structure when the mixed phosphorus source is used. The amount of such linkages subject to attack by hydrolysis is decreased by controlling the proportions of orthophosphoric and pyrophosphoric, without adversely affecting the enhancement of catalytic activity for the production of maleic anhydride which is effected by the use of the mixed phosphorus source.

In general, the process of the present invention includes the steps of:

(a) introducing at least one pentavalent vanadium compound into an organic liquid capable of reducing at least a portion of the vanadium to a valence state of +4;

(b) effecting reduction of at least a portion of the vanadium to a valence state of +4;

(c) contacting the vanadium with a mixed phosphorus source prior or subsequent to effecting said reduction, wherein said mixed phosphorus source comprises about 75–90 weight percent orthophosphoric acid and about 10–25 weight percent pyrophosphoric acid;

(d) comminuting the catalyst precursor resulting from steps (a) through (c);

(e) introducing the catalyst precursor into water prior or subsequent to said comminuting to form an aqueous slurry; and (f) spray drying said slurry to form microspheroidal catalyst particles.

The catalysts prepared by the above process are particularly effective in the fluid bed oxidation of 4-carbon atom hydrocarbons such as n-butane, n-butenes, 1,3 butadiene or mixtures thereof with molecular oxygen or an oxygen-containing gas in the vapor phase to produce high yields of maleic anhydride with high selectivity. Essentially all the product produced in this oxidation process is maleic anhydride, with only minor amounts of lower acids being detected.

DETAILED DESCRIPTION OF THE INVENTION

In the process for the preparation of an oxidation catalyst containing the mixed oxides of vanadium and phosphorus, a vanadium compound, particularly a pentavalent vanadium compound, is introduced into a liquid medium capable of reducing the valence state of the vanadium. Suitable vanadium compounds containing pentavalent vanadium include: vanadium pentoxide or vanadium salts, such as ammonium metavanadate and vanadium oxytrihalides. Vanadium pentoxide is preferred.

In one embodiment of the invention, the pentavalent vanadium containing compound is at least partially solubilized in the liquid medium. To aid in solubilizing the vanadium, it is preferred that the vanadium-containing compound which is introduced into the liquid medium have a small particle size, and methods for further reducing particle size of the vanadium compound while in the liquid medium, such as by ball milling the initial suspension of vanadium in the liquid medium, may be employed.

The liquid medium used in the process of the present invention may comprise an aqueous medium which contains reducing agents including but not limited to HCl or HBr, finely divided or colloidal metals, or organic reducing agents such as alcohols, acids, aldehydes, ethers, ketones and the like. The liquid medium preferably comprises an organic liquid capable of reducing at least a portion of the vanadium to a valence state of +4. The organic liquid medium may comprise alcohols, carboxylic acids, aldehydes, ketones, ethers, epoxides, oxygenated olefinic organic liquids, halogenated olefinic organic liquids and mixtures thereof, among others. It is preferred that the liquid medium comprise and be maintained an essentially anhydrous organic liquid. The liquid medium is preferably a solvent for and is relatively inert towards the mixed phosphorus component.

After the pentavalent vanadium compound is introduced into the liquid medium, reduction of the vanadium is effected either prior to or subsequent to the addition of the mixed phosphorus component to the liquid medium. The reduction is effected preferably by heating the resulting reaction medium, with stirring if desired. Preferred vanadium and phosphorus oxide catalysts for the oxidation of 4-carbon atom hydrocarbons to maleic anhydride contain vanadium in an average valence state of about +3.5 to about +4.6. This average valence state is achieved when at least a portion of the pentavalent vanadium introduced into the reaction mixture is reduced to the +4 state. The average valence state of the vanadium is reduced preferably to about +4.1.

After partial reduction of the vanadium, in one embodiment of the invention, unsolubilized vanadium-containing compounds are removed from the reaction mixture. While the unsolubilized vanadium-containing compounds generally contain some portion of vanadium in a valence state less than +5, the greater portion of vanadium present remains in a +5 valence state. Although it is preferred in this embodiment to remove all unsolubilized vanadium-containing compounds from the liquid medium after effecting reduction of the vanadium, removing all such unsolubilized vanadium-containing compounds having a particle size greater than about 0.1 mm diameter, results in the production of catalysts exhibiting excellent activity for the preparation of maleic anhydride, producing high yields at high selectivity. In a preferred mode of this embodiment of the process of the invention, all unsolubilized vanadium-containing compounds having a particle size greater than about 0.04 to about 0.06 mm diameter are removed. Removal is achieved by conventional means, such as filtration, centrifugation, decantation and the like. After removal of unsolubilized vanadium-containing compounds from the liquid reaction medium, in this embodiment of the invention, the phosphorus component is added to the reaction medium.

The mixed pentavalent phosphorus component according to the present invention comprises a mixture of orthophosphoric acid and pyrophosphoric acid. Optionally, minor amounts of higher polyphosphoric acid may be included. For the preparation of fluid bed catalysts according to the process of the present invention, the mixture should comprise about 75 to about 90 percent orthophosphoric acid, about 10 to about 25 percent pyrophosphoric acid, and 0 to 5 percent triphosphoric acid and higher polyphosphoric acids, percentages being based upon weight of total phosphoric acids. As hydrolysis is a factor in determining the ratio of orthophosphoric acid to pyrophosphoric acid when present in aqueous solution, the above weight ratios are significant provided an extended period of hydrolysis has not occurred to convert the pyrophosphoric acid and higher polyphosphoric acids to the orthophosphoric form.

The mixed phosphorus component is preferably added to the reaction medium in the form of a solution of the phosphorus component in either a component of the liquid reaction medium, or in a liquid capable of yielding the phosphorus component to the liquid reaction medium. After addition of the phosphorus component to the liquid reaction medium, it is preferable to heat the liquid reaction medium, with stirring, if necessary.

In other embodiments of the invention, the phosphorus component, as described above, is added to the liquid medium either before reduction of the pentavalent vanadium substantially occurs, or after such reduction, with no pre-reduction filtration of unsolubilized vanadium compounds. When reduction of the vanadium is effected in the presence of the phosphorus component, the resulting solids dispersed in the liquid medium include the vanadium-phosphorus mixed oxide precursors, to be recovered, dried and calcined.

After formation, the catalyst precursor may be recovered from the liquid reaction medium in which it was prepared by conventional methods, such as evaporation, filtration, centrifugation, decanting, and the like. Preferably, the precursor is dried by heating. Alternatively, the recovered precursor, which is still partially wet with the organic liquid, may be treated with a low boiling solvent such as petroleum ether. In another embodiment, excess preparational reaction media may be substantially removed by vacuum filtration. In yet another embodiment, excess water can be introduced into the precursor containing organic liquid reaction medium, allowing an organic layer to separate from the aqueous layer.

After recovery, the catalyst precursor is introduced into water to form an aqueous slurry. The catalyst precursor generally has a particle size of greater than one micron average diameter before it is comminuted. It is preferred, however, that a substantial portion of the catalyst precursor be reduced in particle size to less than one micron, and preferably less than one half micron average diameter. This step of comminuting may be accomplished before the precursor is recovered from its reaction media, or after recovery. Comminution after recovery can be effected either prior or subsequent to introduction into water. For example, dried catalyst precursor particles may be dry milled, such as by ball milling, or the catalyst precursor aqueous slurry may be ball milled.

The catalyst precursor preferably should be uncalcined when introduced into water. Substantial contacting of the calcined vanadium phosphorus mixed oxide catalyst with water (at less than 100° C.) reduces the activity of the catalyst, particularly if calcined in air.

The solids content of the catalyst precursor containing aqueous slurry should be adjusted to about 25 to about 60 weight percent. The catalyst precursor-containing aqueous slurry is then spray dried to form uniform, microspheroidal particles having a particle size in the range of about 20 to about 300 microns, generally between 20 to about 240 microns. The resulting catalysts are commercially acceptable for fluidization, having at least about 80% of the particle within the range of about 30 to about 80 microns. Spray drying may be accomplished by methods known in the art.

The catalyst precursor may contain promoter elements, including but not limited to U, Co, Mo, Fe, Zn, Hf, Zr or mixtures thereof. These may be incorporated into the catalyst precursor in any of the methods known in the art, such as inclusion via the liquid reaction medium prior to or after reduction of the vanadium.

Inert diluents or supports may be added to the fluid bed catalyst, such as by addition of the diluent or support to the aqueous slurry prior to spray drying.

Catalysts suitable for the production of maleic anhydride from 4-carbon atom hydrocarbons generally have a phosphorus to vanadium ratio of about 3:1 to about 0.5:1. Preferred is a P/V ratio of about 1.2:1. These catalysts preferably exhibit an average valence for vanadium within the range of +3.5 to +4.6.

The catalyst may be calcined in air or an oxygen-containing gas at a temperature of 250° C. to 600° C. for a period of up to 5 hours or more. One method of calcination of the catalyst is accomplished by heating the catalyst in a mixture of steam and air or air alone over the catalyst at a temperature of about 300° C. to 500° C. for a period of about 1 to 5 hours. The catalyst may also be calcined either in the presence of hydrocarbon, in an inert gas or both. The fluid bed catalyst prepared by the process of the present invention may be utilized in oxidation type fluid bed reactors known in the art.

The hydrocarbon reacted to form maleic anhydride may be n-butane, n-butenes, 1,3-butadiene, or a mixture thereof. Preferred is the use of n-butane or a mixture of hydrocarbons that are produced in refinery streams. The molecular oxygen is most conveniently added as air, but synthetic streams containing molecular oxygen are also suitable. In addition to the hydrocarbon and molecular oxygen, other gases may be added to the reactant feed. For example, steam or nitrogen could be added to the reactants.

The ratio of the reactants may vary widely and are not critical. The ratio of molecular oxygen to the hydrocarbon may range from about 3 to about 30 moles of oxygen per mole of hydrocarbon. Preferred oxygen/- hydrocarbon ratios are about 4 to about 20 moles of oxygen per mole of hydrocarbon.

The reaction temperature may vary widely and is dependent upon the particular hydrocarbon and catalyst employed. Normally, temperatures of about 250° C. to about 600° C. are employed with temperatures of 325° C. to 500° C. being preferred. The contact time may be as low as a fraction of a second or as high as 50 seconds. The reaction may be conducted at atmospheric, superatmospheric or subatmospheric pressure. Operation at superatmospheric pressure is preferred, from greater than one atmosphere to about three atmospheres.

SPECIFIC EMBODIMENTS OF THE INVENTION

Catalyst Precursor

It is critical for the preparation of fluid bed vanadium phosphorus mixed oxide catalysts, spray dried from an aqueous slurry of catalyst precursor, that the catalyst precursor not be excessively soluble in water. Solubility should be less than 10%, preferably being less than 5% when subjected to the test procedure set forth below. The solubility of the catalyst precursor in water, among other properties, influences the viscosity of the aqueous slurry to be spray dried. It is preferred that the slurry to be spray dried have a low viscosity, to facilitate processibility.

EXAMPLES 1-7

Vanadium phosphorus mixed oxide catalyst precursors were prepared using phosphoric acid mixtures of various ratios by the following procedure. One mole of $V_2O_5$ (90.5 g) was suspended in one liter isobutanol, to which was added a solution of 1.2 moles of phosphorus in 0.5 liters isobutanol. The ortho/pyro/tri-phosphoric acid weight ratio for each is set fourth in Tables I and II below. The slurry was refluxed for about 20 hours, cooled, filtered and thereafter dried at about 130° C. until free flowing.

The solubility of the catalyst precursors in water was tested by slurrying 50 g catalyst precursor in 300 ml water, and heating to about 100° C.

The results of the solubility tests are listed in Table I. It should be noted that the solubility test is an accelerated test, more strenuous than normal processing conditions. Solubilities reported for this test are therefore, greater than would be expected under normal conditions.

The relative viscosity of the precursor-containing aqueous slurries of catalyst precursors in Examples 1-7 having about 50% solids content are also listed in Table I. As can be seen from Table I, catalyst precursors prepared with a mixture of about 75-90% orthophosphoric acid, and about 10-25% pyrophosphoric acid as the phosphorus source exhibit the most satisfactory processing characteristics.

TABLE I

| Example No. | Phosphoric Acid Ratio Ortho/Pyro/Tri | H$_2$O Solubility (weight %) | Relative Viscosity |
|---|---|---|---|
| 1 | 100/—/— | 1 | high |
| 2 | 87/11.5/1.5 | 3 | low |
| 3 | 87/11.5/1.5 | 3 | low |
| 4 | 73/24/3 | 12 | medium |
| 5 | 73/24/3 | 12 | medium |
| 6 | 60/35/5 | 35 | — |

TABLE I-continued

| Example No. | Phosphoric Acid Ratio Ortho/Pyro/Tri | H$_2$O Solubility (weight %) | Relative Viscosity |
|---|---|---|---|
| 7 | 54/41/5 | — | high |

The catalyst precursors prepared in Examples 1-7 were calcined in air at 400° C. for 1 hour, pelleted to 3/16 inch (0.48 cm) diameter and tested for activity in a 20 cc fixed bed reactor consisting of a length of stainless steel tubing having an outer diameter of about 1.3 cm. The reactor was heated with a split stainless steel block furnace. Flasks for receiving the product maleic anhydride were mounted in ice water, and tail gases were routed to a Carle Analytical Gas Chromatograph III for analysis. Reaction conditions and results of the tests run are described in Table II. The results of the tests reported in Tables II and III are stated in terms as follows:

$$\text{Single Pass Yield} = \frac{\text{Moles of Maleic Anhydride Formed}}{\text{Moles of Butane Fed}} \times 100$$

$$\text{Total Conversion} = \frac{\text{Moles of Butane Reacted}}{\text{Moles of Butane Fed}} \times 100$$

$$\text{Selectivity} = \frac{\text{Single Pass Yield}}{\text{Total Conversion}} \times 100$$

TABLE II

Preparation of Maleic Anhydride from N-Butane Using Catalysts of the Formula $V_1P_{1.2}O_x$

| Example No. | Temperature °C. | % Yield Maleic Anhydride | % Total Conversion |
|---|---|---|---|
| 1 | 421 | 51.8 | 88.8 |
| 2 | 406 | 53.2 | 88.8 |
| 3 | 412 | 55.4 | 91.8 |
| 4 | 419 | 42.3 | 87.3 |
| 5 | 411 | 49.6 | 83 |
| 6 | 403 | 51.4 | 88.4 |
| 7 | 404 | 56.1 | 85.7 |

Fluid Bed Catalysts

The fluid bed catalysts described in Examples 8-24, below, were used to produce maleic anhydride from n-butane in a 440 cc fluid bed reactor consisting of about a 61 cm length of stainless steel tubing having an outer diameter of about 3.8 cm, having a stainless steel sparger at the bottom of the tube to act as a gas (air) distributor, with an axial 0.64 cm outer diameter thermowell and a separate hydrocarbon inlet at the bottom of the tube. The reactor was fitted with internal gas redistributing baffles. Gas preheating and reactor temperature control was accomplished by placement of the reactor unit in a thermostated fluidized sand bath.

Flasks for receiving the product maleic anhydride were air cooled, and tail gases were routed to a Carle Analytical Gas Chromatograph III for analysis. Reaction conditions and results of the tests run are described in Table III. The throughput of hydrocarbon feed in the production of maleic anhydride, or the working rate imposed upon the catalyst, is designated in the tables as WWH, or weight of feed/weight of catalyst/hour.

EXAMPLES 8-14

Fluid bed catalysts having the formula $V_{1.0}P_{1.2}O_x$ (where x=number of oxygens needed to satisfy the valence requirements of the other elements was prepared according to the following procedure. Catalyst precursor was prepared by introducing 7.276 kg $V_2O_5$, and about 10.5 kg mixed phosphoric acid (including about 1.2 kg $H_2O$) into 120 liters isobutanol with stirring, and refluxing the resulting slurry for about 6 hours. The mixed phosphoric acid source contained about 87% orthophosphoric acid, 11.5% pyrophosphoric acid and about 1.5% triphosphoric acid based upon total weight of phosphoric acid. The slurry was cooled, the catalyst precursor recovered by filtration and dried for about 3 hours at 150° C.

herein. These have been provided merely to demonstrate operability, and the selection of methods of preparation of the vanadium and phosphorus-mixed-oxide containing catalyst precursors, promoter elements if any, inert diluents or supports, if any, methods of comminution, hydrocarbon feedstocks and reaction conditions can be determined from the total specification disclosure provided without departing from the spirit of the invention herein disclosed and described, the scope of the invention including modifications and variations that fall within the scope of the attached claims.

TABLE III

FLUID BED (440 CC) PRODUCTION OF MALEIC ANHYDRIDE FROM n-BUTANE USING $V_{1.0}P_{1.2}O_x$ CATALYSTS

| Example No. | Temperature °C. Bath | Temperature °C. Bed | Ratio Air/ Hydrocarbon | Contact Time (Sec.) | WWH | % Conversion | Maleic Anhydride % Yield | Maleic Anhydride % Selectivity | Time On Stream (hrs.) |
|---|---|---|---|---|---|---|---|---|---|
| $V_{1.0}P_{1.2}O_x$ Catalyst | | | | | | | | | |
| 8 | 386 | 394 | 29.0 | 6.7 | 0.020 | 97.9 | 60.0 | 61.2 | 78 |
| 9 | 394 | 405 | 29.5 | 6.8 | 0.020 | 83.3 | 55.8 | 67.0 | 145 |
| 10 | 403 | 411 | 36.4 | 9.1 | 0.020 | 82.2 | 57.6 | 70.0 | 196 |
| 11 | 426 | 440 | 26.4 | 8.6 | 0.028 | 89.8 | 56.4 | 62.8 | 246 |
| 12 | 425 | 439 | 29.8 | 8.8 | 0.024 | 91.0 | 55.9 | 61.4 | 334 |
| 13 | 425 | 440 | 28.9 | 8.9 | 0.024 | 93.3 | 57.1 | 61.2 | 429 |
| 14 | 425 | 442 | 22.4 | 10.8 | 0.026 | 92.4 | 53.6 | 58.0 | 479 |
| 80% $V_{1.0}P_{1.2}O_x$/20% $SiO_2$ | | | | | | | | | |
| 15 | 376 | 380 | 61.7 | 6.0 | 0.014 | 88.0 | 41.5 | 47.1 | 43 |
| 16 | 405 | 414 | 27.6 | 5.7 | 0.031 | 78.3 | 46.8 | 59.8 | 257 |
| 17 | 431 | 439 | 27.4 | 5.6 | 0.030 | 76.2 | 46.8 | 61.4 | 527 |
| 18 | 438 | 446 | 28.4 | 8.5 | 0.019 | 94.4 | 50.7 | 53.7 | 720 |
| 19 | 438 | 446 | 28.8 | 8.2 | 0.019 | 93.1 | 51.0 | 54.7 | 882 |
| 20 | 438 | 446 | 28.1 | 8.5 | 0.019 | 91.5 | 51.9 | 56.7 | 957 |
| 21* | 438 | 449 | 28.5 | 10.9 | 0.024 | 94.6 | 50.9 | 53.8 | 1,074 |
| 22* | 438 | 449 | 31.2 | 11.1 | 0.023 | 95.6 | 46.0 | 48.2 | 1,285 |
| 23* | 438 | 451 | 27.0 | 8.9 | 0.031 | 86.4 | 48.1 | 55.7 | 1,375 |
| 24* | 439 | 451 | 24.0 | 10.0 | 0.031 | 86.3 | 46.2 | 53.6 | 1,400 |

*Reactor outlet pressure 10 PSIG

The dried catalyst precursor was ballmilled for about 5.5 hours and 3000 g comminuted catalyst precursor was thereafter introduced into 3667 g water with stirring. The resulting slurry was spray dried to yield uniform, microspheroidal catalyst particles.

EXAMPLES 15–24

Fluid bed catalyst having the formula 80 wt.% $V_{1.0}P_{1.2}O_x$/20 wt. % $SiO_2$ was prepared according to the following procedure. About 2.5 kg dry, comminuted catalyst precursor, prepared as in Examples 8–14 was introduced into about 2.6 kg water, containing about 1.8 kg Nalco 1034A silica sol (trade designation of Nalco Chemical Co.), with stirring. The resulting slurry was spray dried to yield uniform, microspheroidal catalyst particles. Results of the fluid bed (440 cc) production of maleic anhydride from n-butane using the catalyst of Examples 8–24 are listed in Table III.

As can be seen from the results listed in Tables I through III, fluid bed catalysts containing the mixed oxides of vanadium and phosphorus, prepared from a mixed ortho/pyro-phosphoric acid source, may be prepared according to the process of the present invention. Such catalysts may be spray dried from an aqueous slurry of catalyst precursor to form fluidizable microspheroidal catalyst particles, minimizing catalyst precursor solubility in water and slurry viscosity. The catalysts prepared according to the process of the present invention are useful in the production of maleic anhydride from 4 carbon atom hydrocarbons.

Thus it should be apparent to those skilled in the art that the subject invention accomplishes the objects set forth above. It is to be understood that the subject invention is not to be limited by the examples set forth

We claim:

1. A process for the production of maleic anhydride by the oxidation of 4-carbon hydrocarbons with molecular oxygen or an oxygen containing gas in a fluid bed reactor at a reaction temperature of about 250° C. to 600° C. in the presence of a microspheroidal, fluidizable catalyst containing the mixed oxides of vanadium and phosphorus, wherein said catalyst is prepared by
   (a) introducing at least one pentavalent vanadium compound into an organic liquid capable of reducing at least a portion of the vanadium to a valence state of +4;
   (b) effecting reduction of at least a portion of the vanadium to a valence state of +4;
   (c) contacting the vanadium with a mixed phosphorus component prior or subsequent to effecting said reduction, wherein said mixed phosphorus component comprises about 75–90 weight percent orthophosphoric acid and about 10–25 weight percent pyrophosphoric acid;
   (d) comminuting the catalyst precursor resulting from steps (a) through (c);
   (e) introducing the catalyst precursor into water prior or subsequent to said comminuting to form an aqueous slurry; and
   (f) spray drying said slurry to form microspheroidal catalyst particles.

2. A process as in claim 1, comprising the additional step of calcining the microspheroidal catalyst particles.

3. A process as in claim 1, wherein said mixed phosphorus component comprises about 80–90 weight percent orthophosphoric acid, about 10–20 weight percent pyrophosphoric acid and 0-3 weight percent triphosphoric acid.

4. A process as in claim 1, wherein said organic liquid is essentially anhydrous.

5. A process as in claim 1, wherein reduction of said vanadium is effected by heating the vanadium-containing liquid medium.

6. A process as in claim 1 wherein said mixed phosphorus source additionally comprises up to 5 weight percent triphosphoric acid.

7. A process as in claim 1 wherein said catalyst additionally contains promoter elements selected from the group consisting of U, Co, Mo, Fe, Zn, Hf, Zr and mixtures thereof.

8. A process as in claim 1, wherein said catalyst precursor is substantially dried prior to introducing the catalyst precursor into water.

9. A process as in claim 1, wherein a substantial portion of said catalyst precursor is comminuted to a particle size of less than about one micron average diameter.

10. A process as in claim 1, wherein said aqueous slurry has a solids content of about 25 to about 60 weight percent.

11. A process as in claim 1 wherein a substantial portion of said microspheroidal particles have a particle size of less than 300 microns.

12. A process as in claim 1 wherein a substantial portion of said microspheroidal particles have a particle size of about 20 microns to about 240 microns.

13. A process as in claim 1 wherein said reduction of vanadium is effected in the presence of the mixed phosphorus component.

14. A process as in claim 1 wherein n-butane is reacted.

15. A process as in claim 1 wherein said oxidation occurs at a reactor pressure greater than one atmosphere.

16. A process as in claim 1 wherein said reaction temperature is about 325° C. to 500° C.

* * * * *